United States Patent [19]
van der Kooy et al.

[11] Patent Number: 6,117,675
[45] Date of Patent: Sep. 12, 2000

[54] RETINAL STEM CELLS

[75] Inventors: Derek van der Kooy, Toronto; Roderick McInnes, Ontario; Bernard Chiasson, York; Vincenzo Tropepe, Toronto, all of Canada

[73] Assignee: HSC Research and Development Limited Partnership, Toronto, Canada

[21] Appl. No.: 08/937,967

[22] Filed: Sep. 25, 1997

Related U.S. Application Data

[60] Provisional application No. 60/026,698, Sep. 25, 1996.

[51] Int. Cl.[7] .............................. C12N 5/06; C12N 5/08; C12N 5/10
[52] U.S. Cl. ........................ 435/354; 435/366; 435/377; 435/379; 435/384; 435/385; 435/455
[58] Field of Search ................................ 435/325, 172.3, 435/379, 354, 366, 377, 384, 385, 455

[56] References Cited

FOREIGN PATENT DOCUMENTS

| | | |
|---|---|---|
| WO/93/01275 | 1/1993 | WIPO . |
| WO 94/09119 | 4/1994 | WIPO . |
| WO 94/10292 | 5/1994 | WIPO . |
| WO 94/16718 | 8/1994 | WIPO . |
| WO 95/13364 | 5/1995 | WIPO . |

OTHER PUBLICATIONS

Kohn.,Clin. Exp. Immunol. 107:54–57 (1997).
Anchan et al., "EGF and TGFα Stimulate Retinal Neuroepithelial Cell Proliferation In Vitro", Neuron, 6:923–937 (1991).
Anglade et al., "The Diagnosis and Management of Uveitis", Drugs, 49(2):213–223 (1995).
Bloom et al., "The Diagnosis of Cytomegalovirus Retinitis", Anals of Internal Medicine, 109(12):963–968 (1988).
Cepko et al., "Cell fate determination in the vertebrate retina", PNAS 93:589–595 (1996).
Craig et al., "In Vivo Growth Factor Expansion of Endogenous Subependymal Neural Precursor Cell Populations in the Adult Mouse Brain", The Journal of Neuroscience, 16(8):2649–2658 (1996).
Dyment, "Eye Disorders", Pharmacy Practice, 29–32 (1989).
Holt et al., "Giant Papillary Conjunctivitis", Pharmacist, 68–80 (1992).
Jeffery, "The albino retina: an abnormality that provides insight into normal retinal development" TINS 20(4):165–169 (1997).
Lehndahl et al., "CNS sTem cells Express a New Class of Intermediate Filament Protein" Cell 60:585–595 (1990).
Lightman, "Uvetis: Management"The Lancet 338:1501–1503 (1991).
Lillien et al., "Control of proliferation in the retina: temporal changes in responsiveness to FGF and TGFα", Development, 115:253–266 (1992).
Liu et al., "Developmental Expression of a Novel Murine Homeobox Gene (Chx 10): Evidence for Roles in Determination of the Neuroretina and Inner Nuclear Layer" Neuron 13:377–393 (1994).
Luke et al., "Transplantation—an update" On Continuing Practice 17(2):35–39 (1990).
Morshead et al., "Neural Stem Cells in the Adult Mammalian Forebrain: A Relatively Quiescent Subpopulation of Subependymal Cells" Neuron 13:1071–1082 (1994).
Opas et al., "bFGF–Induced Transdifferentiation of RPE to Neuronal Progenitors is Regulated by the Mechanical Properties of the Substratum" Development Biology 161:440–454 (1994).
Park et al., "Induction of Retinal Regeneration in Vivo by Growth Factors" Developmental Biology 148:322–333 (1991).
Weiss et al., "Is there a neural stem cell in the mammalian forebrain" TINS Review 19(9):1–13 (1996).

*Primary Examiner*—Johnny F. Railey, II
*Attorney, Agent, or Firm*—Clark & Elbing LLP

[57] ABSTRACT

The invention relates to stem cells isolated from the retina of mammals and retinal cells differentiated from these stem cells. The invention also relates to a method of isolating retinal stem cells and inducing retinal stem cells to produce retinal cells. Retinal stem cells may also be induced in vivo to produce retinal cells. The invention also includes pharmaceuticals made with retinal stem cells or retinal cells which may be used to restore vision lost due to diseases, disorders or abnormal physical states of the retina. The invention includes retinal stem cell and retinal cell culture systems for toxicological assays, for isolating genes involved in retinal differentiation or for developing tumor cell lines.

17 Claims, 3 Drawing Sheets

RETINAL STEM CELLS

CROSS REFERENCE TO RELATED APPLICATIONS

This application claims the benefit of U.S. Provisional Application No. 60/026,698 filed Sep. 25, 1996, which is incorporated by reference herein in its entirety.

FIELD OF THE INVENTION

The invention relates to stem cells isolated from the retina of mammals. The invention includes a method for stimulating proliferation of endogenous retinal stem cells in vivo and pharmaceutical compounds that stimulate proliferation of retinal stem cells. The invention also relates to a method for isolating retinal stem cells, uses for the stem cells and pharmaceutical compositions containing the stem cells or their progeny. The invention can be used to treat individuals having retinal diseases, disorders or abnormal physical states. The invention includes retinal stem cells and retinal cell culture systems for toxicological assays, drug development, isolating genes involved in retinal differentiation or for developing tumor cell lines.

BACKGROUND OF THE INVENTION

Vision loss may be caused by disease or damage to the retina of the eye. The retina consists of a specialized layer of cells at the back of the eye where light entering the eye is sensed as an image. These cells normally respond to all aspects of the light emitted from an object and allow perception of color, shape and intensity. The types of cells located in the retina include retinal pigment epithelial ("RPE") cells, rod cells, cone cells, bipolar cells, amacrine cells, horizontal cells, Mueller cells, glial cells, and retinal ganglion cells.

When normal retinal function is impaired, it may lead to a loss of color perception, blind spots, reduced peripheral vision, night blindness, photophobia, decreased visual acuity or blindness. For example, acquired immunodeficiency virus ("AIDS") patients may suffer cytomegalovirus retinitis which is caused by spread of the cytomegalo virus to the retina (Bloom et al., Medicine, 109(12): 963–968 (1988)). This and other infectious processes can lead to loss of visual field, decreased visual acuity, and blindness.

Uveitis is an inflammation of the eye which can affect the retina and can lead to decreased visual acuity. Its effects on the retina include inflamed or leaking vasculature which may appear as perivascular exudation or haemorrhage, oedema of the retina, chorioretinal lesions, neovascularization or inflammatory changes in the peripheral retina. (Anglade et al., Drugs, 49(2):213–223 (1995)).

Cancers of the retina also impair vision. One example is retinoblastoma, which is a childhood type of cancer. Other diseases may occur through age-related macular degeneration.

Many different genetic diseases lead to retinal damage and blindness. A relatively common example is retinitis pigmentosa ("RP"), which affects one person in four thousand worldwide. Patients with RP have normal vision for one or more decades, and then experience progressive loss of vision due to the premature death of rod or cone cells. Blindness may result. Other types of retinal degenerations (retinal dystrophies) may result from the programmed death of other retinal cell types.

Physical damage to retinal cells may also occur through retinal detachment which leads to retinal degeneration and blindness.

The therapeutic strategies for treating loss of vision caused by retinal cell damage vary, but they are all directed to controlling the illness causing the damage, rather than reversing the damage caused by an illness by restoring or regenerating retinal cells. As one example, the treatments of uveitis are drawn from the knowledge of changes in the retinal environment when inflammation occurs. Corticosteroids, such as prednisone, are the preferred drug of treatment. However, these drugs are immunosuppressants with numerous side effects. As well, the systemic immunosuppression may have significant negative effects on the development of children as well as on adults in poor health such as the elderly and patients with chronic disease. These patients must try alternate drugs such as alkylating agents or antimetabolites which also have side effects. Clearly, patients with eye diseases remain vulnerable to sustaining permanent damage to the retinal cells, even if drug treatments are available.

There are no known successful treatments for RP and other retinal dystrophies. There are also no treatments which regenerate new cells endogenously or which transplant healthy tissue to the retina. Even if it were possible to develop some form of transplantation, it would be subject to the same problems that accompany transplants in other organ systems. These include:

in many cases, implants provide only temporary relief as the symptoms associated with the disease often return after a number of years, rejection by the patient of foreign tissue, adverse reactions associated with immunosuppression (immunosuppression is needed to try to help the patient accept the foreign tissue), the inability of a sufficient number of cells in the tissue being implanted to survive during and after implantation, transmitting other diseases or disorders may be transmitted to the patient via the implant, and the results may not justify the costs and efforts of a complex procedure.

Thus, there is currently no way to reverse permanent damage to the retina and restore vision. Drug treatments focus on treating the illness and its symptoms to prevent further damage to the retina. There is a need to reverse damage to the retina and restore vision by endogenously generating new retinal cells or transplanting retinal cells.

In tissues other than the eye, stem cells are used as a source for alternative treatments of disease or injury to tissues. Stem cells are undifferentiated cells that exist in many tissues of embryos and adult mammals. In embryos, blastocyst stem cells are the source of cells which differentiate to form the specialised tissues and organs of the developing fetus. In adults, specialised stem cells in individual tissues are the source of new cells which replace cells lost through cell death due to natural attrition, disease or injury. No stem cell is common to all tissues in adults. Rather, the term "stem cell" in adults describes different groups of cells in different tissues and organs with common characteristics.

Stem cells are capable of producing either new stem cells or cells called progenitor cells that differentiate to produce the specialised cells found in mammalian organs. Symmetric division occurs where one stem cell divides into two daughter stem cells. Asymmetric division occurs where one stem cell forms one new stem cell and one progenitor cell.

A progenitor cell differentiates to produce the mature specialized cells of mammalian organs. In contrast, stem cells never terminally differentiate (i.e. they never differentiate into a specialized tissue cells). Progenitor cells and stem cells are referred to collectively as "precursor cells". This term is used when it is unclear whether a researcher is dealing with stem cells or progenitor cells or both.

Progenitor cells may differentiate in a manner which is unipotential or multipotential. A unipotential progenitor cell is one which can form only one particular type of cell when it is terminally differentiated. A multipotential progenitor cell has the potential to differentiate to form more than one type of tissue cell. Which type of cell it ultimately becomes depends on conditions in the local environment as such as the presence or absence of particular peptide growth factors, cell-cell communication, amino acids and steroids. For example, it has been determined that the hematopoietic stem cells of the bone marrow produce all of the mature lymphocytes and erythrocytes present in fetuses and adult mammals. There are several well-studied progenitor cells produced by these stem cells, including three unipotenltial and one multipotential tissue cell. The multipotential progenitor cell may divide to form one of several types of differentiated cells depending on which hormones act upon it.

Weiss et al, Review, 1–13 (1996) summarises the five defining characteristics of stem cells as the ability to:

Proliferate: Stem cells are capable of dividing to produce daughter cells.

Exhibit self-maintenance or renewal over the lifetime of the organism: Stem cells are capable of reproducing by dividing symmetrically or asymmetrically. Symmetric division is a source of renewal of stem cells. Symmetric division leads to increases in the number of stem cells. Asymmetric division maintains a consistent level of stem cells in an embryo or adult mammal.

Generate large number of progeny: Stem cells may produce a large number of progeny through the transient amplification of a population of progenitor cells.

Retain their multilineage potential over time: Stem cells are the ultimate source of differentiated tissue cells, so it is a characteristic that they retain their ability to produce multiple types of progenitor cells, which will in turn develop into specialized tissue cells.

Generate new cells in response to injury or disease: This is essential in tissues which have a high turnover rate or which are more likely to be subject to injury or disease, such as the epithelium or blood cells.

Thus, the key features of stem cells are that they are multipotential cells which are capable of long-term self-renewal over the lifetime of a mammal.

There is great potential for the use of stem cells as substrates for producing healthy tissue where pathological conditions have destroyed or damaged normal tissue. For example, stem cells may be used as a target for in vivo stimulation with growth factors or they may be used as a source of cells for transplantation.

There has been much effort to isolate stem cells and determine which peptide growth factors, hormones and other metabolites influence stem cell renewal and production of progenitor cells, which conditions control and influence the differentiation of progenitor cells into specialized tissue cells, and which conditions cause a multipotent progenitor cell to develop into a particular type of cell.

In several tissues, stem cells have been isolated and chlaracterised to develop new therapies to repair or replace damaged tissues. For example, stem cells have been isolated from the mammalian brain (Reynolds et al., Science 255:107 (1992)). WO 93/01275, WO 94/16718, WO 94/10292 and WO 94/09119 describe uses for these cells. WO 95/13364 reports that delivery of growth factors to the ventricles of the central nervous system ("CNS") stimulates neural stem cells to proliferate and produce progenitor cells which will develop into neurons, oligodendrocytes or astrocytes. All of these publications restrict the isolation or use of adult stem cells to the brain (in particular, the tissue around the brain ventricles, the subependyma, which is the remnant of the embryonic brain germinal zone). There is no reported isolation of a retinal stem cell from the adult peripheral nervous system ("PNS") of a mammal. There is no evidence for production of new neurons within the adult eye, so those knowledgeable about stem cells would not suspect that stem cells would be produced in the retina.

Stem cell cultures also provide useful assay cultures for toxicity testing or for drug development testing. Toxicity testing is done by culturing stem cells or cells differentiated from stem cells in a suitable medium and introducing a substance, such as a pharmaceutical or chemical, to the culture. The stem cells or differentiated cells are examined to determine if the substance has had an adverse effect on the culture. Drug development testing may be done by developing derivative cell lines, for example a pathogenic retinal cell line, which may be used to test the efficacy of new drugs. Affinity assays for new drugs may also be developed from the stem cells, differentiated cells or cell lines derived from the stem cells or differentiated cells.

The stem cells also provide a culture system from which genes, proteins and other metabolites involved in cell development can be isolated and identified. The composition of stem cells may be compared with that of progenitor cells and differentiated cells in order to determine the mechanisms and compounds which stimulate production of stem cells, progenitor cells or mature cells.

It would be useful if stem cells could be identified and isolated in areas of the CNS and PNS outside the adult brain, such as the retina. Medical treatments could then be developed using those stem cells. To date, no person has suggested that a retinal precursor cell in a mammal even exists beyond the embryonic stage of development, (a retinal stem cell would self-renew to exist from embryonic development to adulthood). There are retinal precursor cells in the embryonic eye which exhibit some of the characteristics of stem cells. However, since it is believed that these cells do not persist into the adult eye, this would indicate, by definition, that the embryonic precursors could only be retinal progenitor cells and not real retinal stem cells. The prior art teaches that it is highly unlikely that there is a retinal stem cell. Most of the prior art involves studies of embryonic precursor cells isolated from the mammalian eye (see e.g. Anchan et al., Neuron 6:923–936, (1991), Lillien et al., Development 115:253–266 (1992); Cepko et al., PNAS 93:589–595 (1996)). Precursor cells can be multipotential, however they usually have more restricted phenotype potential than stem cells. They also have only limited self-renewal capability. Anchan et al., Neuron 6:923–936, (1991), and Lillien et al., Development 115:253–266 (1992) both isolated embryonic retinal precursors in culture, however, they did not discuss retinal stem cells nor establish that retinal stem cells exist and can be isolated and purified. In summary, before this invention, no one expected that stem cells even existed in the retina or that the cardinal features of stem cells, self renewal and multipotentiality, could be found in those cells.

Current medical and surgical drug treatments are inadequate for restoring vision lost when retinal cells are damaged, so the potential clinical applications of pharmaceutical compounds containing retinal stem cells or to stimulate endogenous proliferation of retinal stem cells are tremendous. Retinal stem cells would have the potential to act as in vivo targets for stimulation by growth factors in order to produce healthy tissue. This may be done, for example, by injecting growth factors or genetically engineered cells which secrete growth factors into the eye. Some very preliminary work in this area was clone by Park et al., Developmental Biology 148:322–333 (1991). They stimulated retinal pigment epithelial cells in embryonic birds with FGF2 in vivo to regenerate a neural retina. However, this was in birds, not mammals, and only in embryonic birds. Moreover, the cells of the regenerated neuroretina formed in these chicks were not in their normal location. Thus, the photoreceptors, normally closest to the brain, were located farthest from it, and ganglion cells were closest to the brain. Thus, there is a clear need to develop techniques to safely and effectively target stem cells in vivo in mammals with growth factors in order to regenerate healthy eye tissue. The eye is easily accessible surgically or by injection, and it would be helpful if this accessibility could be exploited by targeting retinal stem cells in areas of damage.

It would also be useful if stem cells were discovered that could proliferate in the absence of growth factors.

A need also exists for a pharmaceutical composition containing retinal cells for transplantation in which (1) the composition is accepted by the patient, thus avoiding the difficulties associated with immunosuppression, (2) the composition is safe and effective, thus justifying the cost and effort associated with treatment, (3) the composition provides long term relief of the symptoms associated with the disease, (4) the composition is efficacious during and after transplantation. There is a clear need to develop retinal stem cell cultures which can act as a source of cells that are transplantable in vivo in order to replace damaged tissue.

There is also a need for retinal stem cell cultures or retinal cell cultures which may be used in toxicity testing, drug development and to isolate new genes and metabolites involved in cell differentiation. There is also a need for retinal cell cultures which may be used to develop derivative cell lines, such as retinoblastoma cell culture lines, for studying cancer or other diseases, disorders or abnormal states.

SUMMARY OF THE INVENTION

The invention provides for stem cells isolated from the mammalian retina and retinal cells differentiated from these stem cells.

This invention overcomes the needs outlined above in that it provides a method for stimulating stem cells of the retina to proliferate in vivo to produce differentiated retinal cells. Proliferation is induced by administering one or more growth factors to the retina. Proliferation is also induced by administering genetically engineered cells which secrete growth factors into the eye.

The retinal stem cells may also be used as sources of transplantable tissue, as they can be removed from the donor and transplanted into a recipient either before or after differentiation into retinal cells. This invention also satisfies the needs outlined above in that the retinal stem cells of this invention (1) are accepted by the patient because they can be taken from the patient's own retina, (2) are safe in that the patient is not receiving cells or tissue from another source, (3) are effective in that the retinal stem cells can be differentiated into retinal cells for implantation and survive during and after implantation, and (4) offer the potential to provide long term relief of the symptoms of conditions associated with loss of one or more retinal cell types.

The invention also provides cell cultures which may be used in toxicity testing, drug development and the isolation of new genes and metabolites involved in cell differentiation.

Accordingly, it is an object of the invention to provide retinal stem cells which are isolated and purified from the retina of a mammal. Retinal cells are then differentiated from the retinal stem cells. Retinal cells which may be produced from the stem cells are rod cells, cone cells, bipolar cells, amacrine cells, retinal ganglion cells, retinal pigment epithelial cells, Mueller cells, horizontal cells or glial cells.

The retinal stem cells are characterized by the presence of Chx 10 protein, which is a marker for precursor cells.

The retinal stem cells may be transformed or transfected with a heterologous gene. The growth or differentiation retinal stem cells may be stimulated by a trophic factor.

The retinal stem cells and the retinal cells are useful in toxicity testing, drug development testing, developing derivative cell lines, and isolating genes or proteins involved in cell differentiation.

It is another object of the invention to provide a pharmaceutical composition for use in implant therapy consisting of the retinal stem cells and retinal cells in a pharmaceutically acceptable carrier, auxiliary or excipient. The invention also relates to a method of treating a disease, disorder or abnormal state of the retina by stimulating proliferation of retinal stem cells. According to one embodiment of this invention, a growth factor is introduced to retinal pigment epithelial cells. In the method, the disease may be one of blindness, cytomegalovirus retinitis, uveitis, glaucoma, macular degeneration, retinitis pigmentosa, retinal degeneration, retinal detachment and cancers of the retina. An individual suffering from a degenerative disease, disorder or abnormal physical state of the retina may also be treated by implanting the retinal stem cells or retinal cells into the eye of the individual.

Another object of the invention is to provide a method for isolating and purifying retinal stem cells from the retina of a mammal by taking a sample of the retina from the mammal, dissociating the sample into single cells, placing the cells in culture, isolating the cells which survive in culture and differentiating the cells which survive in culture into retinal cells.

In another embodiment of the invention, where the mammal is a human and is suffering from a disease, disorder or abnormal physical state of the eye, the method includes implanting the retinal stem cells or retinal cells differentiated from the retinal stem cells, into the eye of the human. Where the mammal is a human and is not suffering, from a disease, disorder or abnormal physical state of the eye, the method includes implanting the retinal stem cells or retinal cells differentiated from the retinal stem cells into a second human who is suffering from the disease, disorder or abnormal physical state. The disease, disorder or abnormal physical state which may be treated may be one of the group consisting of blindness, cytomegalovirus retinitis, uveitis, glaucoma, macular degeneration, retinitis pigmentosa, retinal degeneration, retinal detachment and cancers of the retina.

Another object of the invention is to provide a kit, containing at least one type of cells selected from a group consisting of the retinal stem cells and the retinal cells. The kit may be used for the treatment of a disease, disorder or abnormal physical state of the eye.

The cells of the invention may also be used in a method for identifying a substance which is toxic to retinal stem cells and retinal cells, by introducing the substance to a retinal stem cell culture or a retinal cell culture differentiated from a retinal stem cell culture, and determining whether the cell culture is adversely affected by the presence of the substance, is employed.

The cells of the invention may also be used in a method for identifying a pharmaceutical which may be used to treat a disease, disorder or abnormal state of the eye, by introducing the pharmaceutical to a retinal stem cell culture or a retinal cell culture differentiated from a retinal stem cell culture, and determining whether the culture is affected by the presence of the pharmaceutical.

The invention also includes a method of stimulating proliferation of retinal stem cells, comprising introducing a growth factor to retinal pigment epithelial cells. The growth factor is selected from a group consisting of EGF, FGF2, NGF, CNTF, BDNF, FGF4, FGF8 and heparin. Accordingly, another aspect of the invention is a method of treating a disease, disorder or abnormal state of the retina, by stimulating proliferation of retinal stem cells. This is done by introducing a growth factor to retinal pigment epithelial cells. The method of treatment may be used in treating a disease, disorder or abnormal physical state selected from a group consisting of blindness, cytomegalovirus retinitis, uveitis, glaucoma, macular degeneration, retinitis pigmentosa, retinal degeneration, retinal detachment and cancers of the retina.

Pigment granules in individual sphere cells are used to mark the lineage of a retinal cell and the differentiation state of a retinal cell. Retinal stem cells have black pigment granules, progenitor cells have less black pigment granules than retinal stem cells, and neural retinal cells have no black pigment granules.

BRIEF DESCRIPTION OF THE DRAWINGS

The invention will now be described in relation to the figures in which.

DETAILED DESCRIPTION OF THE INVENTION

This invention discloses the isolation of a stem cell from both embryonic and adult mouse retina as well as adult human retina. This is the first indication that a retinal stem cell is present in the adult mammalian retina. There are embryonic precursor cells but an embryonic precursor cell is not a stem cell as defined in this application because a characteristic of a stem cell is its long term self-renewal (it self-renews throughout the embryonic and adult stage). The prior art teaches that the existence of a retinal stem cell in adult mammals is unlikely. During embryonic and early postnatal development there is a germinal zone (also called a ventricular zone) in the developing eye. There is no obvious remnant of the embryonic retinal germinal (ventricular) zone in the adult mammalian retina and the prior art teaches that the germinal zone disappears postnatally. The ependyma and the retinal-pigment epithelium both arise from their respective ventricular zones and both are generally considered to be post-mitotic epithelial tissue in adult animals. However, the neural retina and subependyma also descend from the ventricular zones of the eye and forebrain, respectively, and differ significantly as the neural retina is generally considered to be largely post-mitotic neuronal tissue whereas the subependyma is a complex of undifferentiated proliferating cells. There is no morphological ventricular tissue to be found in the adult retina.

The stem cells of this invention possess the two key characterizing features of stem cells: they are mutipotential and self-renew. These cells can be stimulated in vivo to generate new retinal cells. The presence of the stem cell in the mature retina suggests that there is no inherent inability to repair any injury or disease to the retina.

It may simply be a matter of administering the right combination of exogenous growth factors to stimulate the adult retinal stem cells to proliferate and differentiate to achieve and replace the compromised parts of the retina. As a result of this discovery, the stem cells may also be cultured in vitro to generate large numbers of new stem cells. The stem cells may also be differentiated by adding growth factors to the culture medium, which provides a source of healthy differentiated retinal tissue cells. The cells of this invention may be used in transplants, toxicity testing, drug development testing, or studies of genes and proteins.

The retinal tissue was dissected using the method of Opas et al., Development Biology, 161:440–454, (1993), as described in Example 1. Single cells were isolated from the embryonic day 14 retina and cultured in the presence of the growth factors, epidermal growth factor ("EGF"), basic fibroblast growth factor ("FGF2") and heparin. The cells were also cultured in the presence of EGF alone. This methodology is described in Example 2.

Figure 3:
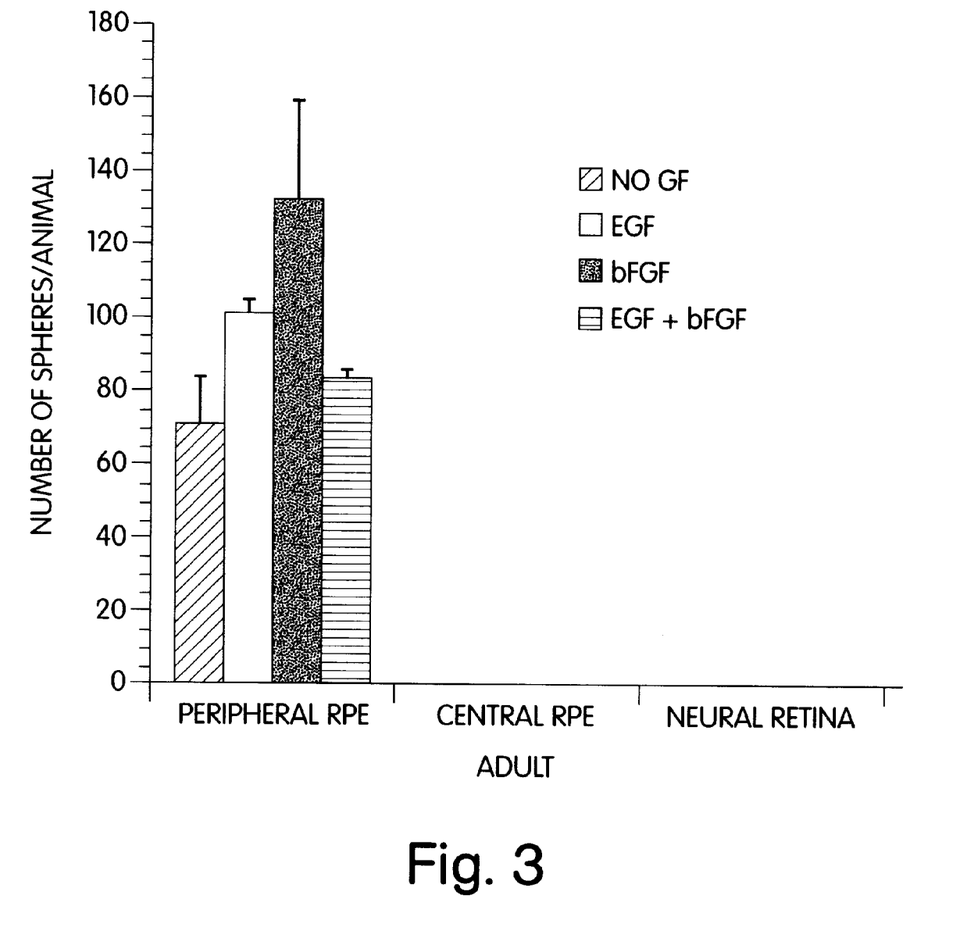
FIG. 3: Retinal stem cells proliferate in the absence of growth factors. EGF & FGF2 facilitate proliferation.

It is now clear that cells do proliferate in the absence of growth factors and that for the most part EGF and FGF2 facilitate proliferation but not extensively (FIG. 3). Our data suggest that FGF2 can cause growth of individual spheres but not so greatly increase the number of spheres generated. It was discovered that these growth factors caused single cells to proliferate to form floating spheres even in serum-free medium. We also isolate and culture a human retinal stem cell (Example 10).

When these spheres were dissociated into single cells, the retinal stem cells self-renewed and proliferated to form new spheres. The cells also exhibited properties that indicated that they were multipotential stem cells.

We identified pan-neuronal and glial markers for retinal sphere derived cells. We identify specific neuronal cell types. Cells which migrate out of plated spheres and begin to differentiate do not express Chx. 10 immunoreactivity as would be expected for all cell types except perhaps bipolar and amacrine cells. When these cells were plated, they differentiated into various neural retinal cell types i.e. they showed retinal specific patterns of differentiation. Furthermore, the proportions of cells produced by differentiation were consistent with these stem cells originating in the retina.

There is clear evidence that the cells of the invention are precursor cells of retinal origin. Some of the cells in the retinal spheres exhibited neural-specific markers, such as the Chx 10 marker (Example 3). The Chx 10 gene was cloned and reagents to it made by Liu et al., Neuron, Vol.

13:377–393 (1994). Chx 10 is a murine polypeptide which is a regulatory protein involved in vertebrate retinal development. It is a marker of neural precursor cells, although it is not clear if it is found in retinal progenitor cells or stem cells. This protein is expressed in early retinal cells in vivo but generally not by telencephalon cells or their progeny. In the mature retina, bipolar and amacrine cells express Chx 10. Some cells in the spheres also tested positively for nesting which is a filamentous protein present only in undifferentiated cells. We also locate other markers which identify retinal precursor cells (Example 9). These markers clearly distinguish retinal stem cells from forebrain stem cells.

Our experiments with mouse retinal cells further indicate that these retinal stem cells come from the ciliary margin of the adult retinal pigment epithelial layer and not the adult neural retinal layer (Example 4).

The stem cells are stimulated to produce differentiated retinal cells in vitro in the presence of growth factors (Example 5). The growth factors are introduced into the site of the stem cells (retinal pigment epithelial cells see—Example 4) to grow the cells in an attempt to repair diseased or damaged retina. The differentiated retinal cells are characterized (Example 8). Production of certain retinal cell types is biased by particular growth factors.

We also administer exogenous growth factor in vivo to stimulate retinal stem cell proliferation (Example 11). The retinal stem cells interface with biomaterials to provide therapies that stimulate axonal cell growth (Example 12).

The pharmaceutical compositions of this invention used to treat patients having degenerative diseases, disorders or abnormal physical states of the eye could include an acceptable carrier, auxiliary or excipient. The compositions can be for topical, parenteral, local, intraocular or intraretinal use.

The pharmaceutical composition can be administered to humans or animals. Dosages to be administered depend on patient needs, on the desired effect and on the chosen route of administration.

The pharmaceutical compositions can be prepared by known methods for the preparation of pharmaceutically acceptable compositions which can be administered to patients, and such that an effective quantity of the cells is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA 1985).

On this basis, the pharmaceutical compositions could include an active compound or substance, such as growth factors, genetically engineered stem cells or retinal cells which secrete growth factor or other substances, in association with one or more pharmaceutically acceptable vehicles or diluents, and contained in buffered solutions with a suitable pH and isoosmotic with the physiological fluids. The methods of combining growth factor or cells with the vehicles or combining them with diluents is well known to those skilled in the art. The composition could include a targeting agent for the transport of the active compound or cells to specified sites within the eye, such as specific cells, tissues or organs.

The invention also relates to the use of the stem cells and progenitor cells of this invention to introduce recombinant proteins into the diseased or damaged retina. The cells act as a vector to transport a recombinant molecule, for example, or to transport a sense or antisense sequence of a nucleic acid molecule. In the case of a recombinant molecule, the molecule would contain suitable transcriptional or translational regulatory elements.

Suitable regulatory elements may be derived from a variety of sources, and they may be readily selected by one of ordinary skill in the art. Examples of regulatory elements include: a transcriptional promoter and enhancer or RNA polymerase binding sequence, a ribosomal binding sequence, including a translation initiation signal. Additionally, depending on the vector employed, other genetic elements, such as selectable markers, may be incorporated into the recombinant molecule.

The recombinant molecule may be introduced into stem cells or retinal cells differentiated from stem cells of a patient using in vitro delivery vehicles such as retroviral vectors, adenoviral vectors, DNA virus vectors, amplicons and liposomes. They may also be introduced into these cells using physical techniques such as microinjection and electroporation or chemical methods such as coprecipitation and incorporation of DNA into liposomes.

Suitable regulatory elements may be derived from a variety of sources, and they may be readily selected by one of ordinary skill in the art. If one were to upregulate the expression of the gene, one would insert the sense sequence and the appropriate promoter into the vehicle. If one were to downregulate the expression of the gene, one would insert the antisense sequence and the appropriate promoter into the vehicle. These techniques are known to those skilled in the art.

The pharmaceutical compositions could also include the active compound or substance, such as the stem cells of this invention or retinal progenitor cells or differentiated cells derived from those stem cells, in association with one or more pharmaceutically acceptable vehicles or diluents, and contained in buffered solutions with a suitable pH and iso-osmotic with the physiological fluids. The methods of combining cells with the vehicles or combining them with diluents is well known to those skilled in the art. The composition could include a targeting agent for the transport of the active compound to specified sites within the eye, such as specific cells, tissues or organs.

EXAMPLE 1

Dissection of Retina and Retinal Pigment Epithelium (RPE)

We considerably narrowed the area from which the retinal stem cell originates in the adult eye. The pigmented cells associated with the ciliary margin is the only area from which retinal spheres can be isolated in the adult animal. Dissections done on younger animals (embryonic or early post-natal) typically include the entire RPE. The cells of this invention may be used with biomaterials in a method of medical treatment of ocular dysfunction or disease. The dissection of the adult and embryonic neural retinal and RPE layers was done similarly to the method described for dissecting chick embryo retina in Opas et al., Development Biology, 161:440–454, (1993) in artificial cerebrospinal fluid (aCSF) containing 124 mM NaCl, 5 mM KCl, 1.3 mM $MgCl_2$, 2 mM $CaCl_2$, 26 mM $NaHCO_3$, and 10 mM D-glucose (pH 7.4) previously aerated (15 min) with 95% $O_2$–5% $CO_2$ at room temperature. RPE cultures were prepared by enucleating mouse embryos or adults, removing anterior portions of the eye (including the lenticular and corneal tissue) and by making an incision through the sclera to facilitate the removal of the vitreous, retina and associated vasculature. The retinal cups, with exposed RPE, were incubated in a sterile dispase solution (Collaborative Research) at 30–32° C. for 10 min, and then in a sterile high $Mg^{2+}$, low $Ca^{2+}$ aCSF solution at 37° C. for 10 min in the presence of trypsin (1.3 mg/mL), hyaluronidase (0.66 mg/mL), and kyneurinic acid (0.1 mg/mL). In the case of embryonic tissue, the retinal cups were taken from dispase and separated from the basement membrane. The high $Mg^{2+}$, low $Ca^{2+}$ aCSF solution, in the presence of trypsin, hyaluronidase and kyneurinic acid was not used for embryonic tissue (only adult tissue). The RPE was separated from its basement membrane (and associated choroidal tissue and vasculature) and placed in serum-free media (described below). The neural retinal tissue was prepared in a similar manner.

EXAMPLE 2

Isolation and Culturing of Retinal Stem Cells in the Presence of Growth Factors

Retinal cells were dissociated and cultured in the presence of growth factors according to the methods described in Morshead et al., Neuron, Vol. 13:1071–1082 (1994) and Reynolds et al., 1993. After dissection and enzymatic treatment, neural retina and RPE tissues were cut into 1 mm sections and transferred into serum-free culture medium (described below) containing 0.7 mg/mL trypsin inhibitor (Boehringer-Mannheim) to stop the enzymatic reaction and mechanically dissociated (trituration) with a fire-polished Pasteur pipette. The cell suspension was then centrifuged at 150×g for 5 min, the media was aspirated and the pellet was resuspended in fresh serum-free media only.

The dissociated cells were plated in noncoated 35 mm culture dishes (NUNC 96 well plates) at desired densities (determined by Trypan blue exclusion) with serum-free medium containing 20 ng/mL EGF (UBI; purified from mouse sub-maxillary gland), or 10 ng/mL FGF2 (UBI; human recombinant) with heparin (2 ug/mL; UBI). The serum-free medium was composed of DMEM/F12 (1:1) (Gibco) and contained a salt and hormone mix of insulin (25 ug/mL), transferrin (100 ug/mL), progesterone (20 nM), Putrescine (60 uM), selenium chloride (30 nM), glucose (0.6%), glutamine (2 mM), sodium bicarbonate (3 mM), and HEPES buffer (5 mM). Single cells proliferated in response to the defined growth factors in serum-free media to form floating spheres. These retinal stem cells were passaged by mechanical dissociation of spheres into single cells. The number of spheres were counted in each 96 well culture dish after a 5–10 day incubation period.

This procedure was used to obtain retinal cell cultures from mouse embryo and adult mouse. We use similar procedures to obtain retinal stem cell cultures from human embryo and adult humans.

We performed a passage of the retinal stem cells and showed that 1) the stem cell is passageable and 2) the cell division characteristics reveal that it is an asymmetrically dividing cell as opposed to a symmetrically dividing cell like forebrain cells. A single sphere always give rise to one sphere. We harvested these cells from adults and embryos which shows that they are long lived. The passage in culture of cells identified in both the embryonic and adult retina establishes this cell as a stem cell—the ability to self-renew throughout the life of the animal.

The retinal spheres were different from the neurospheres generated by embryonic and adult telencephalic neural stem cells in that the retinal spheres expressed high levels of Chx 10 (see Example 3), a marker of neural precursor cells that is a gene product demonstrated to be essential for normal development of the mammalian eye (Burmeister et al., Nature Genetics 12:376–384, 1996).

EXAMPLE 3

ChX 10 Marker Occurs in Retinal Stem Cells

EGF, FGF2 and heparin together induced the proliferation of retinal stem cells in serum-free medium, which produced a sphere of undifferentiated precursor cells. EGF alone in serum-free medium also produced undifferentiated precursor cells. These spheres were not immunoreactive for glial fibrillary acidic protein (GFAP) (an intermediate filament protein specific for astrocytes), neuron-specific enolase (a neuron-specified enzyme), or myelin basic protein (MBP) (a cell surface protein specific to oligodendrocytes). The spheres were, however, immunoreactive for nesting (characterized by Lehndahl et al., Cell 60:585 (1990)) which is an intermediate filament protein found in undifferentiated CNS cells. The precursor cells were also irnmunoreactive for the Chx 10 protein marker (characterized by Liu et al., Neuron, Vol. 13, 377–393 (1994); Burmeister et al. Nature Genetics 12:376–384, 1996). Chx 10 marker is a homcobox gene that is normally expressed in vivo by all retinal precursors. Chx 10 can be found in forebrain stem cell derived spheres although it is in lesser quantity than it is in retinal stem cells. Chx 10 is also only expressed in very limited regions of the forebrain. The mature cell types that differentiate from these precursor cells were predominantly not immunoreactive for nesting or Chx 10. When differentiated in vitro, separate cells from the spheres derived from retinal stem cells expressed glial and at least one pan neuronal marker.

EXAMPLE 4

Figure 1:
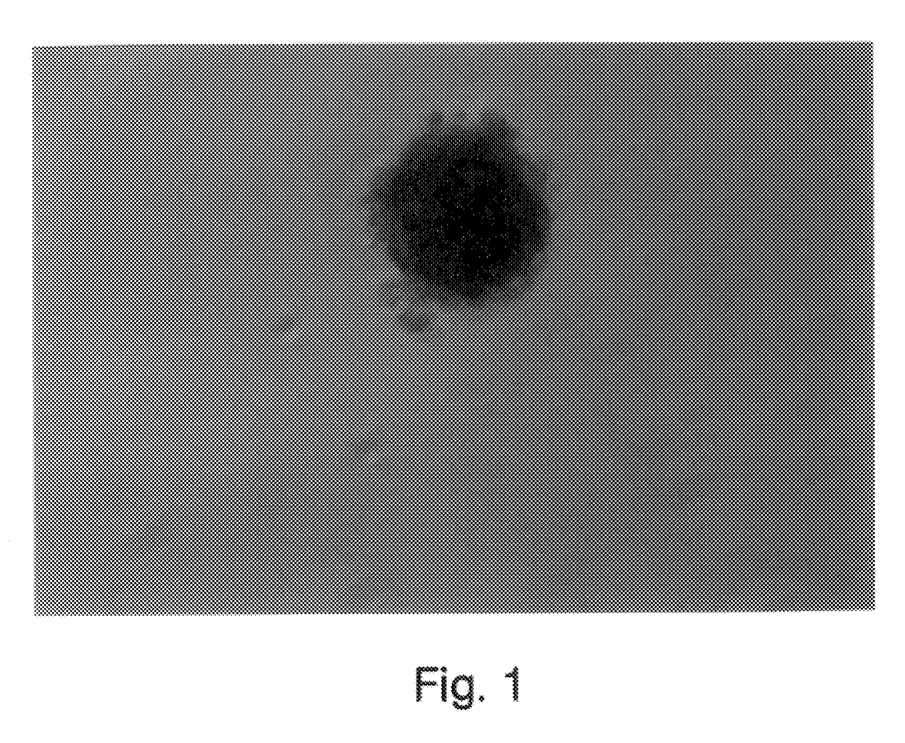
FIG. 1: Spheres formed from self-renewal of single retinal stem cells from the retinal pigment epithelial layer of the adult mouse eye. When grown in culture, only black spheres formed initially which indicated that the retinal stem cells came from the retinal pigment epithelial layer.
Figure 2:
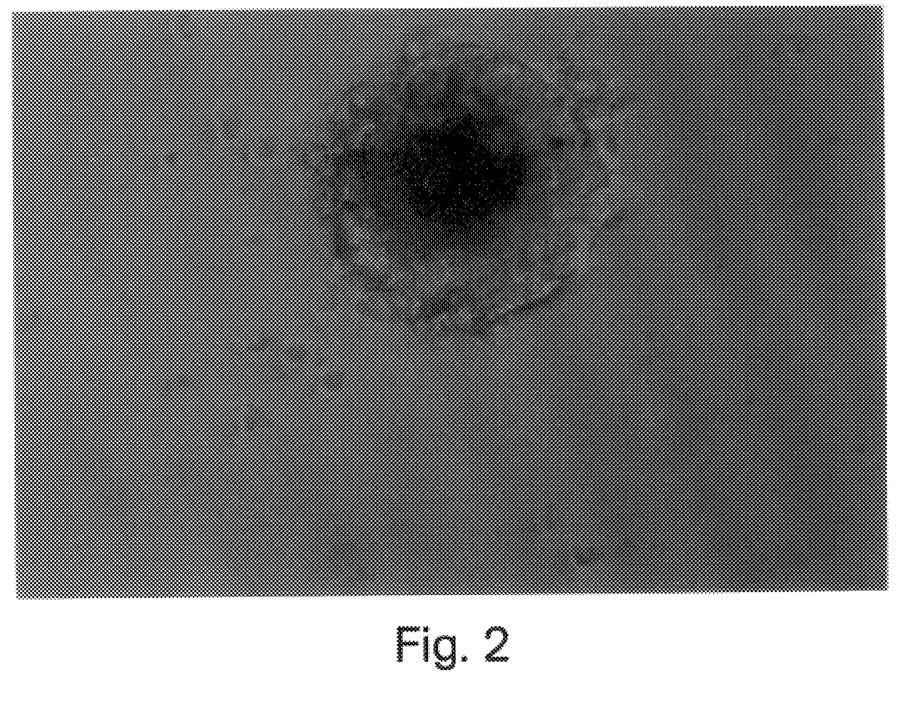
FIG. 2: After 2–3 days, the spheres depicted in FIG. 1 both contained black and white cells, indicating that the black stem cells produced white progenitor cells of the neural retina.

Adult Retinal Stem Cell Originates from Adult Retinal Pigment Epithelial Population These experiments determined the origin of the adult retinal stem cell. The retina consists of the inner neural retinal layers and an outer cell monolayer of RPE cells. The RPE cells in pigmented mice are visibly pigmented (melanin granules), whereas the neural retinal cells are essentially nonpigmented. We separated the retinal layers (previously described in Example 1) and found that the retinal stem cells (retinal spheres) came from the RPE layer in vitro. The RPE stem cells initially proliferated to form small spheres of primarily pigmented cells (FIG. 1), but after several more days of growth in serum-free media/growth factors, the pigmented spheres started to produce nonpigmented progeny (FIG. 2). The nonpigmented cells are neural retinal cells.

The result of this experiment suggests that the density of pigment granules in individual cells within a sphere (isolated from a single pigmented cell in the RPE layer) provide an independent marker for the lineage and/or differentiation state of a retinal cell: stem cells are heavily pigmented, different more restricted progenitor cells have smaller and variable numbers of pigment granules (perhaps distributed in different cellular compartments), and differentiated neural retinal cells are nonpigmented. This is an effective way to do lineage analysis and will be used in conjunction with specific retinal cell type markers to determine the correlation between the relative density of retinal stem cell-derived progenitors and the onset of retinal cell type specific differentiation. For example, utilizing immunocytochemistry to determine the temporal pattern of retinal cell differentiation from sphere-derived cells to determine: (1) how pigmentation levels and distribution correlate with the stage of differentiation as detected by cell-specific antibodies such as neurofilament (ganglion cells), rhodopsin (rod cells), HPC (horizontal cells), VC1.1 (amacrine cells), and GFAP (Mueller glia); and (2) if the temporal order of emerging differentiated retinal cell types is conserved in vitro, with ganglion cells differentiating first, etc.

EXAMPLE 5
Stimulation of Proliferation of the Embryonic and Adult Eye Stem Cell We stimulate proliferation of the adult and embryonic retinal stem cell in a chemically defined serum-free medium in the presence of growth factors. Basic fibroblast growth factor (FGF2), epidermal growth factor (EGF), nerve growth factor (NGF), ciliary neurotrophic factor (CNTF), brain-derived neurotrophic factor (BDNF), insulin-like growth factor (IGF-1) and stem cell factor (SCF) are all tested separately to stimulate proliferation of the adult and embryonic retinal stem cell to produce spheres. Similarly, various combinations of these growth factors are used to determine the extent of combinatorial effects between growth factors to facilitated retinal stem cell proliferation and sphere formation in vitro.

Stimulating production of Chx 10 may encourage the generation of retinal precursors. For example, growth factors may be used to stimulate Chx 10 production which encourages later differentiation of more specific retinal stem cells (for example, bipolar cells).

EXAMPLE 6
Proliferation of the Embryonic and Adult Eye Stem Cell in the Absence of Growth Factors The retinal stem cell can be isolated from the adult mouse in serum free conditions independent of any growth factors (including insulin). This is shown in FIG. 3. The neural stem cells of the adult and embryonic forebrain do not proliferate in the absence of growth factors. In fact, of the many growth factors that have been utilized to try to stimulate the generation of forebrain neurospheres, only three factors have thus far been successfully used. EGF, FGF2 and IGF-1 have all been shown to stimulate the generation of neurospheres from forebrain tissue. Thus, the retinal cell is a cell type that can proliferate and be passed in the absence of any growth factors something that no other primary mammalian cell type is capable of doing.

EXAMPLE 7
Proliferation of the Embryonic and Adult Eye Stem Cell in the Absence of Growth Factors Another clear difference between forebrain neurospheres and retinal stem cells is that the retinal stem cell is pigmented whereas the forebrain neurosphere is not. The biochemistry involved with pigmentation is important in the proliferative capacity of the stem cell (Jeffrey, T.I.N.S., 20:4:165–169 (1997)) because we get differences in the size and number of retinal spheres generated from pigmented mice or rats compare to their non-pigmented counterparts. Spheres generated from non pigmented cells are smaller and fewer in number.

EXAMPLE 8
Characterization of Differentiated Retinal Cell Types

We determine which differentiated cell types are produced with various growth factors (and combinations) in culture. Identification of one growth factor (or combination of specific growth factors) which biases the production of one specific differentiated retinal cell type is extremely useful in trying to repair eye injuries in humans that involve primarily one specific cell type. Using immunocytochemistry or in situ hybridization, we determine the presence of differentiated retinal cell types using established markers such as neurofilament (ganglion cells), HPC (horizontal cells), Chx 10 (bipolar cells), VC1.1 (amacrine cells), rhodopsin (rod cells), and GFAP (Mueller glia) (Liu et al., Neuron, Vol. 13,377–393 (1994)).

EXAMPLE 9
New Retinal Markers

We identify other novel markers (besides Chx 10 ) that: (1) identify retinal precursor cells (stem and progenitor cells) and distinguish them from forebrain precursor cells; (2) allow for the identification of genes involved in transition from retinal precursor phenotypes to differentiated retinal phenotypes; and (3) identify genes involved in cell cycle progression during retinal differentiation, using established methods such as differential display. This provides unique markers and targets for ocular cancers. Specific antibodies directed to novel proteins or the presence of novel mRNAs that mark the retinal stem cells or retinal progenitor cells are identified.

EXAMPLE 10
Human Neural Stem Cells

We isolate human neural stem cells in culture from the adult and embryonic retina using the aforementioned media and growth factor conditions, and subsequently utilize aforementioned techniques to determine the identity of stem cell, progenitor cell, and differentiated retinal cell types.

EXAMPLE 11
In vivo Administration of Exogenous Growth Factors

We administer exogenous growth factors in the in vivo adult mammalian eye to stimulate the adult retinal neural stem cell to proliferate in vivo and produce new retinal neurons. We perform this experiment in control mouse eyes and previously injured mouse eyes in vivo to model the recovery of the human eye from injury or disease (procedure set out in Craig et al., The Journal of Neuroscience, 16(8) :2649–2658 (1996)). We perform intraoccular infusions of the aforementioned growth factors and determine retinal cell differentiation using immunohistochemical techniques with the detection of established markers (see Example 8).

The cells of this invention also proliferate in the absence of growth factors, so new retinal neurons may also be produced in vivo in the absence of exogenous growth factors.

EXAMPLE 12
Interface with Biomaterials and Stem Cells to Provide Therapies for Ocular Dysfunction or Disease We deliver encapsulated modified retinal stem cells using biomaterial and genetic engineering technologies (procedures set out in Shiochet et al, 1995). This cell therapy delivers a continuous source of a given factor (of a gene of choice) to the eye. We provide a source of stimulatory or inhibitory factors required for ganglion cell axonal growth into the brain. We also provide more transient therapies using biodegradable materials that in combination with the stem cells require the transient expansion of cell numbers (see Example 11), the reduction of inhibitory components and the increase in stimulatory components to axonal cell growth.

All publications, patents and patent applications are herein incorporated by reference in their entirety to the same extent as if each individual publication, patent or patent application was specifically and individually indicated to be incorporated by reference in its entirety.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

We claim:

1. Retinal stem cells isolated from the retina of a mammal.

2. The retinal stem cells of claim 1, wherein the cells are isolated from a retinal pigment epithelial layer of the retina.

3. The retinal stem cells of claim 1, wherein the mammal is a human or a mouse.

4. Retinal stem cells produced from the retinal stem cells of claim 1.

5. The retinal stem cells of claim 1 or 4, wherein the cells are capable of producing progenitor cells, or progenitor cells and retinal cells.

6. The retinal stem cells of claim 5, wherein the retinal cells are at least one of rod cells, cone cells, bipolar cells, amacrine cells, retinal ganglion cells, retinal pigment epithelial cells, Mueller cells, horizontal cells or glial cells.

7. The retinal stem cells of claim 1 or claim 4, transformed or transfected with a heterologous gene.

8. The retinal stem cells of claim 1 or claim 4, which proliferate without stimulation by growth factors.

9. The retinal stem cells of claim 1 or claim 4, whose growth or production of progenitor cells, or progenitor cells and retinal cells is stimulated by a trophic factor.

10. The retinal stem cells of claim 1 or claim 4, whose growth or production of progenitor cells, or progenitor cells and retinal cells is stimulated by a growth factor.

11. The retinal stem cells of claim 9 or 10, wherein the growth factor or trophic factor is at least one of EGF, FCF2, NGF, CNTF, BDNF, FGF4, FGF8 or heparin.

12. The retinal stem cells of claim 1 or claim 4, wherein the cells are capable of producing progenitor cells that are positive for a Chx 10 marker.

13. A method for obtaining cells from a retinal pigment epithelial layer of a mammal, comprising:
 a) dissociating all or part of the retinal pigment epithelial layer including at least one retinal stem cell into single cells,
 b) culturing the cells in a medium in which a retinal stem cell will produce
 a sphere including retinal stem cells, and
 c) isolating the sphere.

14. The method of claim 13, wherein the sphere further includes retinal progenitor cells.

15. The method of claim 13, further comprising administering a growth factor and/or a trophic factor to the sphere or cells dissociated from the sphere to produce progenitor cells and/or retinal cells, wherein the retinal cells are at least one of rod cells, cone cells, bipolar cells, amacrine cells, retinal ganglion cells, retinal pigment epithelial cells, Mueller cells, horizontal cells or glial cells.

16. A method of preparing progenitor cells or progenitor cells and retinal cells, comprising administering a growth factor and/or a trophic factor to a retinal stem cell so that the retinal stem cell produces progenitor cells, or progenitor cells and retinal cells.

17. Cells obtained according to the method of any of claims 13 to 16.

* * * * *

UNITED STATES PATENT AND TRADEMARK OFFICE
CERTIFICATE OF CORRECTION

PATENT NO.     : 6,117,675
DATED          : September 12, 2000
INVENTOR(S)    : Derek van der Kooy et al.

It is certified that error appears in the above-identified patent and that said Letters Patent is hereby corrected as shown below:

Title page,
Item [56], OTHER PUBLICATIONS, insert the following two references:

-- Chiasson et al., "Eyeballs: Retinal Stem Cells Isolated from the Adult Mouse Retinal Pigment Epithelium," Networks of Centres of Excellence: NeuroScience Network Annual Meeting Abstracts, #23, 1997

Chiasson, Figures and Text from Poster Presentation, Networks of Centres of Excellence: Neuroscience Network Annual Meeting, May 21-24, 1997 --

Column 1,
Line 41, "cytomegalo virus" should be -- cytomegalovirus --

Column 3,
Line 19, "unipotenltial" should be -- unipotential --

Column 5,
Line 7, "clone" should be -- done --

Column 7,
Line 49, "stern" should be -- stem --

Column 8,
Line 2, "-pigment" should be -- pigment --
Line 55, "Chx. 10" should be -- Chx 10 --

Column 12,
Line 14, "irnmunoreactive" should be -- immunoreactive --
Line 17, "homcobox" should be -- homeobox --
Line 12, "nesting" should be -- nestin --
Line 24, "nesting" should be -- nestin --

UNITED STATES PATENT AND TRADEMARK OFFICE
CERTIFICATE OF CORRECTION

PATENT NO.    : 6,117,675
DATED         : September 12, 2000
INVENTOR(S)   : Derek van der Kooy et al.

It is certified that error appears in the above-identified patent and that said Letters Patent is hereby corrected as shown below:

Column 13,
Line 9, "ncurotrophic" should be -- neurotrophic --
Line 40, "Embrvonic" should be -- Embryonic --
Line 55, "ccll" should be -- cell --
Lines 63-64, "neurofilamcnt" should be -- neurofilament --

Column 15,
Line 29, "FCF2," should be -- FGF2, --

Signed and Sealed this

Eleventh Day of February, 2003

JAMES E. ROGAN
*Director of the United States Patent and Trademark Office*